(12) United States Patent
Mikami

(10) Patent No.: US 11,045,071 B2
(45) Date of Patent: Jun. 29, 2021

(54) IMAGE PROCESSING APPARATUS FOR ENDOSCOPE AND ENDOSCOPE SYSTEM

(71) Applicant: OLYMPUS CORPORATION, Hachioji (JP)

(72) Inventor: Toshiaki Mikami, Hino (JP)

(73) Assignee: OLYMPUS CORPORATION, Tokyo (JP)

( * ) Notice: Subject to any disclaimer, the term of this patent is extended or adjusted under 35 U.S.C. 154(b) by 0 days.

(21) Appl. No.: 16/545,280

(22) Filed: Aug. 20, 2019

(65) Prior Publication Data

US 2019/0374087 A1 Dec. 12, 2019

Related U.S. Application Data

(63) Continuation of application No. PCT/JP2017/006645, filed on Feb. 22, 2017.

(51) Int. Cl.
*A61B 1/00* (2006.01)
*G02B 23/24* (2006.01)
(Continued)

(52) U.S. Cl.
CPC ........ *A61B 1/0002* (2013.01); *A61B 1/00045* (2013.01); *A61B 1/00193* (2013.01);
(Continued)

(58) Field of Classification Search
CPC .............. A61B 1/0002; A61B 1/00045; A61B 1/00193; A61B 1/00009; A61B 1/045;
(Continued)

(56) References Cited

U.S. PATENT DOCUMENTS 10,206,554 B2  2/2019 Mizuno
2013/0172675 A1* 7/2013 Yamazaki .............. H04N 9/643
                                                    600/109
(Continued)

FOREIGN PATENT DOCUMENTS

WO   2016059983 A1   4/2016
WO   2016114155 A1   7/2016
(Continued)

OTHER PUBLICATIONS

International Search Report (ISR) dated May 16, 2017 (and English translation thereof) issued in International Application No. PCT/JP2017/006645.
(Continued)

*Primary Examiner* — Thai Q Tran
*Assistant Examiner* — Nienru Yang
(74) *Attorney, Agent, or Firm* — Holtz, Holtz & Volek PC

(57) ABSTRACT

An image processing apparatus for an endoscope includes an image acquisition circuit configured to acquire an image captured by using the endoscope, an interference area setting circuit configured to set, on the image, an interference area having a different characteristic from an observation target in the image, and an interference area corrector configured to perform correction on the image, the correction including a reduction in luminance of the interference area. The interference area setting circuit includes an interference candidate area extractor configured to extract at least one interference candidate area based on the different characteristic from the observation target, and an interference area selector configured to select the interference area from the at least one interference candidate area based on luminance distribution in the at least one interference candidate area.

11 Claims, 12 Drawing Sheets

(51) Int. Cl.
*A61B 1/045* (2006.01)
*A61B 1/05* (2006.01)

(52) U.S. Cl.
CPC ..... *G02B 23/2415* (2013.01); *G02B 23/2484* (2013.01); *A61B 1/00009* (2013.01); *A61B 1/045* (2013.01); *A61B 1/051* (2013.01)

(58) Field of Classification Search
CPC . A61B 1/051; G02B 23/2415; G02B 23/2484
USPC .......................................................... 348/65
See application file for complete search history.

(56) References Cited

U.S. PATENT DOCUMENTS

| | | | |
|---|---|---|---|
| 2014/0081083 A1* | 3/2014 | Morita | A61B 1/00177 |
| | | | 600/109 |
| 2014/0088353 A1 | 3/2014 | Hayama | |
| 2014/0092215 A1* | 4/2014 | Hayama | A61B 1/00045 |
| | | | 348/45 |
| 2017/0086649 A1 | 3/2017 | Mizuno | |
| 2017/0367560 A1 | 12/2017 | Shiraki et al. | |
| 2017/0367566 A1 | 12/2017 | Kikuchi et al. | |

FOREIGN PATENT DOCUMENTS

| | | | | |
|---|---|---|---|---|
| WO | 2016181781 A1 | | 11/2016 | |
| WO | WO-2016181781 A1 | * | 11/2016 | ............. A61B 1/053 |

OTHER PUBLICATIONS

Written Opinion of the International Search Authority dated May 16, 2017 issued in International Application No. PCT/JP2017/006645.

English translation of the International Preliminary Report on Patentability dated Sep. 6, 2019 issued in International Application No. PCT/JP2017/006645.

* cited by examiner

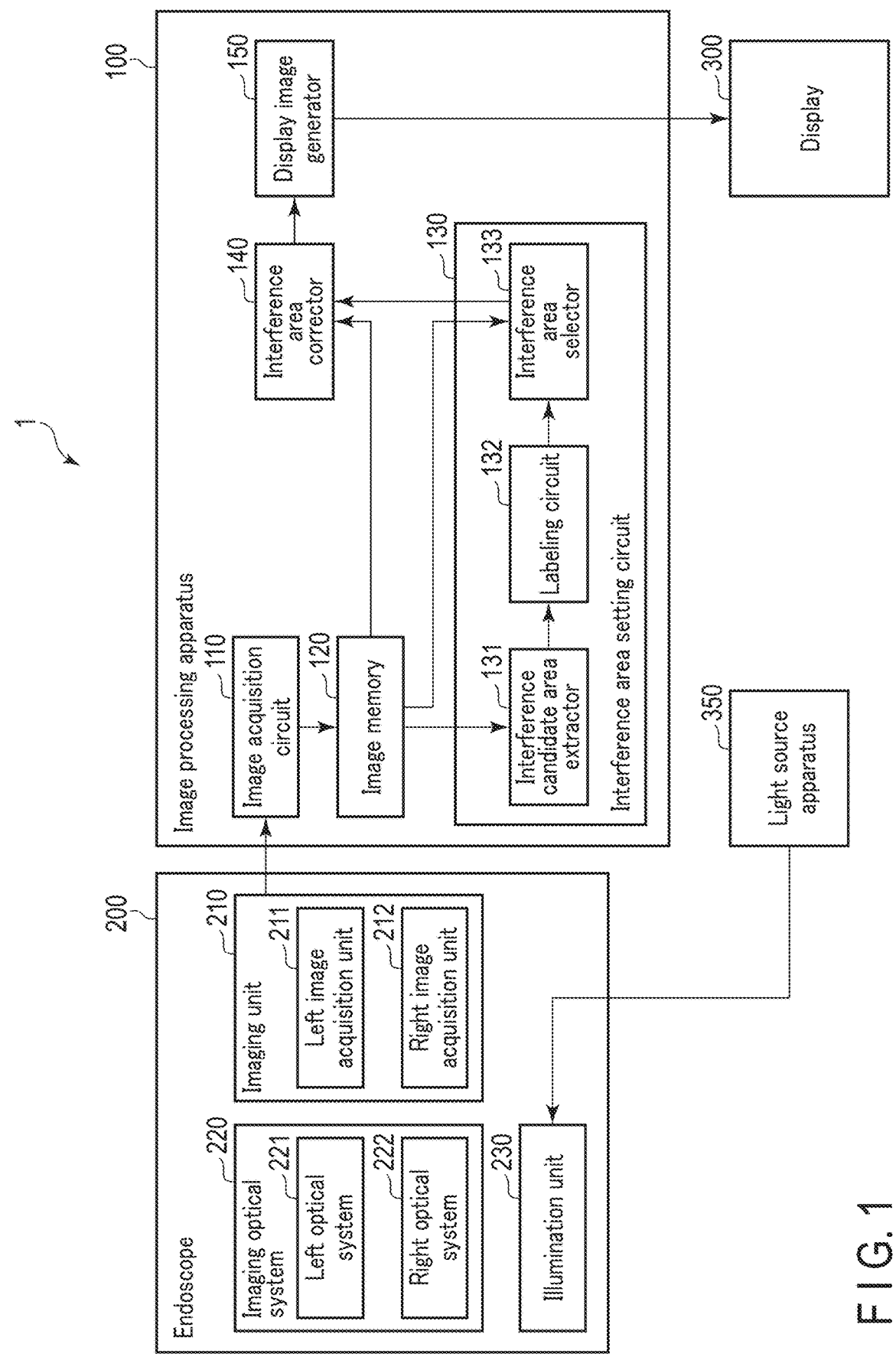
F I G. 1

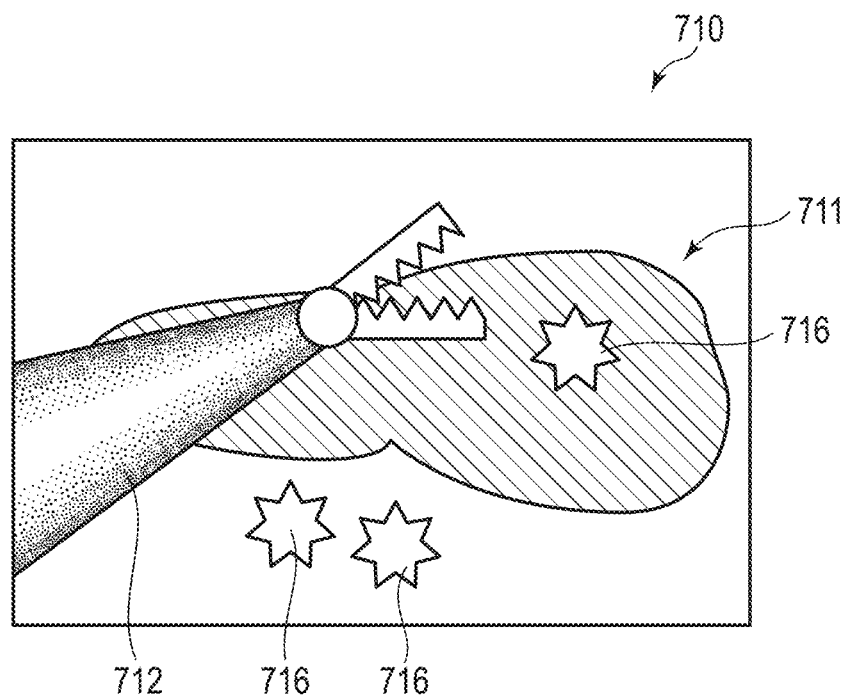
F I G. 5
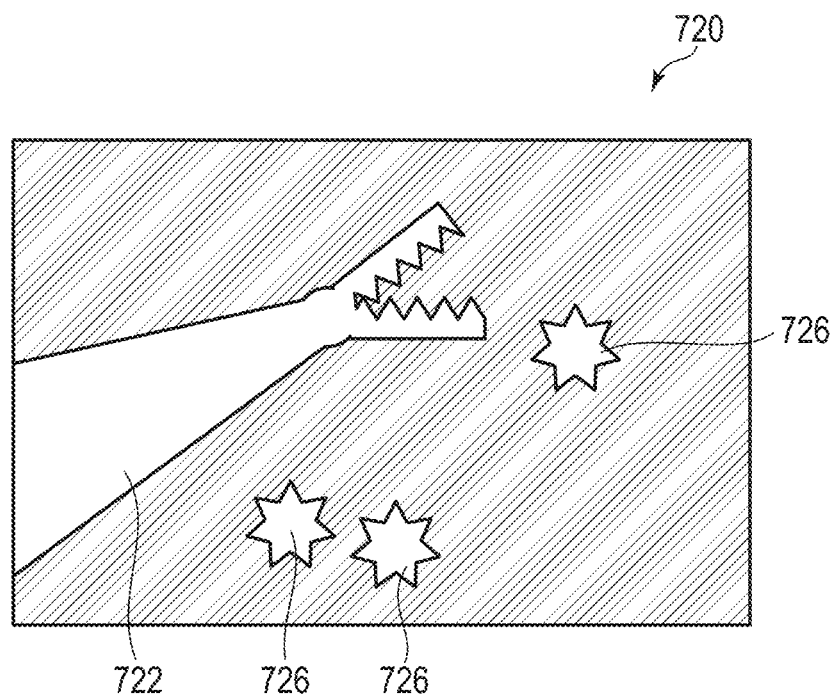
F I G. 6

IMAGE PROCESSING APPARATUS FOR ENDOSCOPE AND ENDOSCOPE SYSTEM

This is a Continuation Application of PCT Application No. PCT/JP2017/006645, filed Feb. 22, 2017, the entire contents of which are incorporated herein by reference.

BACKGROUND

The present invention relates to an image processing apparatus for an endoscope and an endoscope system.

A procedure may be performed using various procedure tools under observation with an endoscope. In such a procedure, when a distal portion of the endoscope which captures an image and a procedure tool that performs the procedure are positioned at a close distance, a range of a capturing view field may be blocked by the procedure tool. Furthermore, illumination light for the capturing may be intensively reflected from the procedure tool, and luminance of the procedure tool may significantly increase on the image. An area with high-luminance is likely to notice, and thus user's eyes are likely to look at the high-luminance area.

In recent years, a three-dimensional endoscope using binocular vision is used in some cases. A subject image acquired by the three-dimensional endoscope is displayed by using a three-dimensional stereoscopic display apparatus such as a three-dimensional (3D) display. When the distal portion of the three-dimensional endoscope and the procedure tool that performs the procedure are positioned at a close distance during capturing by the endoscope, it is not possible to achieve a stereoscopic view of an image displayed by the three-dimensional stereoscopic display apparatus in some cases. In this case, a user feels discomfort. Hence, when the distal portion of the endoscope and the procedure tool that performs the procedure are positioned at a close distance, an area that makes the user feel discomfort is likely to catch the user's eyes. In addition, an image area contained only one of a pair of right and left images which are acquired to obtain disparity can be produced. A space, in which the three-dimensional endoscope is used, has a lumen shape in many cases, a subject that is present in the image area contained in only one of the pair of right and left images has a close distance to the distal portion of the endoscope in many cases. Therefore, a high-luminance area is likely to be produced. Further, the subject is contained in only one of the pair of right and left images, and thus it is not possible to achieve the stereoscopic view of the subject. The user who views the image acquired by the three-dimensional endoscope may feel discomfort.

For example, U.S. Patent Application Publication No. 2014/0088353 discloses a technology related to a reduction in discomfort that a user may feel when using a three-dimensional endoscope. In this technology, an image, in which a procedure tool is captured, and an image, in which the procedure tool is not captured, are acquired. An area, in which the procedure tool is captured, is detected in the image in which the procedure tool is captured, and the image within the area is replaced with an image of an area corresponding to the area in the image in which the procedure tool is not captured. A correspondence of the areas in both images can be acquired by performing area-based matching of both images.

SUMMARY

According to an exemplary embodiment, an image processing apparatus for an endoscope includes an image acquisition circuit configured to acquire an image captured by using the endoscope, an interference area setting circuit configured to set, on the image, an interference area having a different characteristic from an observation target in the image, and an interference area corrector configured to perform correction on the image, the correction including a reduction in luminance of the interference area, wherein the interference area setting circuit includes an interference candidate area extractor configured to extract at least one interference candidate area based on the different characteristic from the observation target, and an interference area selector configured to select the interference area from the at least one interference candidate area based on luminance distribution in the at least one interference candidate area.

According to an exemplary embodiment, an endoscope system includes the image processing apparatus described above, and the endoscope.

Advantages of the invention will be set forth in the description which follows, and in part will be obvious from the description, or may be learned by practice of the invention. Advantages of the invention may be realized and obtained by means of the instrumentalities and combinations particularly pointed out hereinafter.

BRIEF DESCRIPTION OF THE DRAWING

The accompanying drawings, which are incorporated in and constitute a part of the specification, illustrate embodiments of the invention, and together with the general description given above and the detailed description of the embodiments given below, serve to explain the principles of the invention.

FIG. 1 is a block diagram schematically illustrating an example of a configuration of an endoscope system according to embodiments.

FIG. 5 is a view for describing the image process according to the embodiments, that is, a schematic view illustrating an image acquired by an endoscope.

FIG. 6 is a view for describing the image process according to the embodiments, that is, a schematic view illustrating extracted interference candidate areas.

DETAILED DESCRIPTION

First Embodiment

Figure 2:
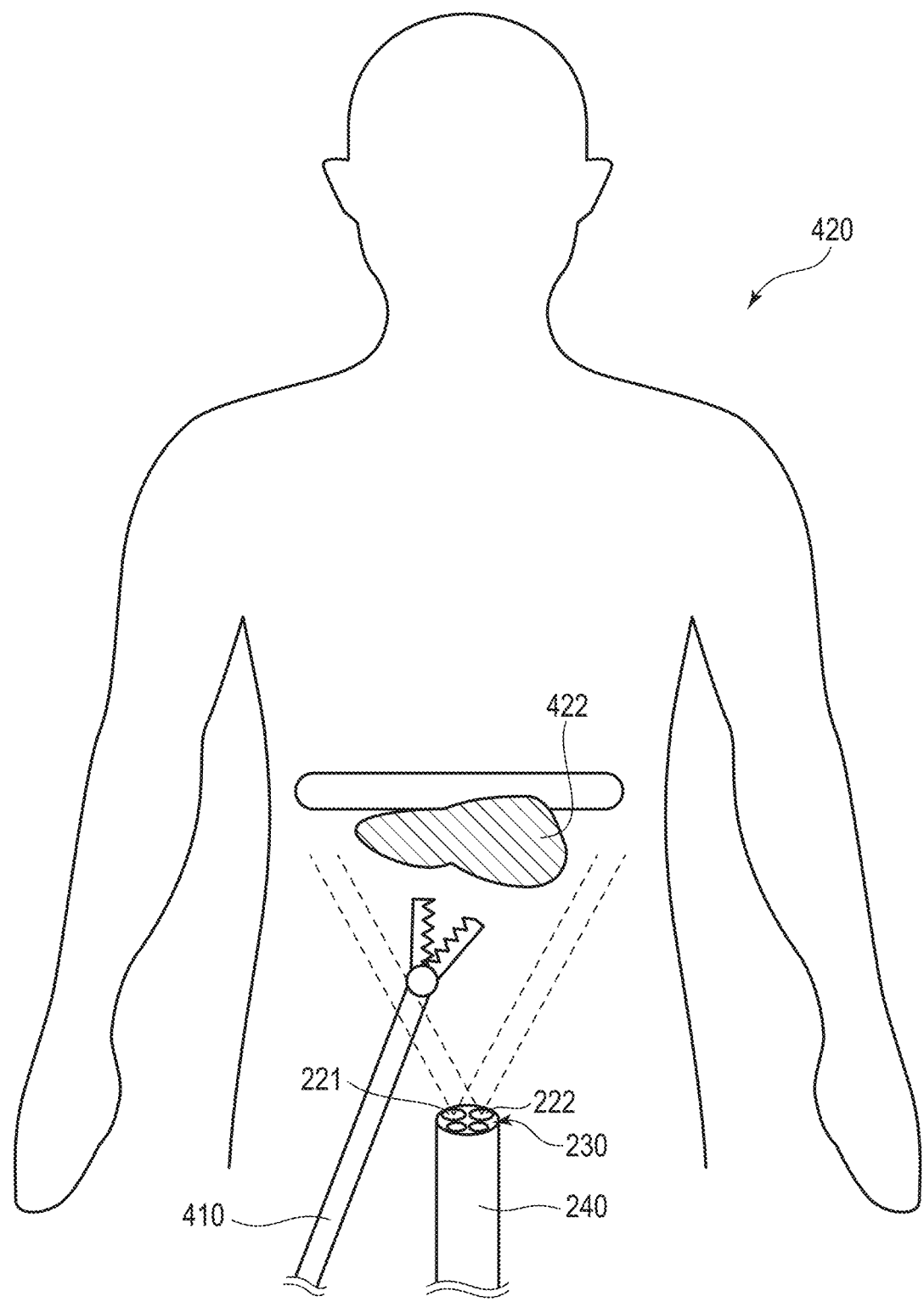
FIG. 2 is a view for describing a mode of use of the endoscope system according to the embodiments.

The first embodiment of the invention is described. The embodiment relates to a three-dimensional (3D) endoscope system. In the endoscope system according to the embodiment, a specific image processing is performed on a video acquired by capturing. In the image processing, an image area that gives some kind of visual discomfort to a user is detected, and correction for reducing the discomfort is performed on the detected image area.

The 3D endoscope includes a stereo camera having a pair of right and left optical systems and an imaging device and captures a pair of right and left subject images. The left image captured by the left optical system and the left imaging device and the right image captured by the right optical system and the right imaging device are obtained as the subject images with disparity approximate to that in a case of the binocular vision of a human. The endoscope system displays an image based on the left image and the right image on the three-dimensional display apparatus, thereby, allowing the user to recognize a three-dimensional image of a subject.

<Configuration of Endoscope System>

An example of a configuration of an endoscope system 1 according to the embodiment is illustrated in a block diagram of FIG. 1. The endoscope system 1 includes an image processing apparatus 100, an endoscope 200, a display 300, and a light source apparatus 350. In the embodiment, the endoscope 200 is described as the 3D endoscope; however, the endoscope 200 is not limited thereto. A part of the endoscope 200 is inserted into an inside of a subject, thereby, capturing an image of the inside of the subject, and the endoscope generates image data of the inside of the subject. The image processing apparatus 100 performs various kinds of image processes or the like on the image data generated by the endoscope 200. The display 300 displays an image processed by the image processing apparatus 100. The light source apparatus 350 is a light source of illumination light for illuminating a range of which an image is captured by the endoscope 200.

For example, the endoscope 200 is a rigid endoscope for surgery and has an insertion part having an elongated shape, the insertion part configured to be inserted into the subject. The endoscope 200 is connected to the image processing apparatus 100 and the light source apparatus 350 via a cable. For example, the insertion part may have a configuration in which a distal portion of the insertion part has a bending portion, which is actively bent, and is bent in a direction that the user wants through an operation by the user.

The distal portion of the insertion part has an imaging unit 210, an imaging optical system 220, and an illumination unit 230. The imaging unit 210 and the imaging optical system 220 both have two right and left systems for acquiring a 3D image. The imaging unit 210 has a left image acquisition unit 211 and a right image acquisition unit 212 that have respective imaging devices such as a CCD image sensor, for example. The imaging optical system 220 includes a left optical system 221, which forms a subject image to be in focus on an imaging plane of the imaging device of the left image acquisition unit 211, and a right optical system 222, which forms a subject image to be in focus on an imaging plane of the imaging device of the right image acquisition unit 212. The illumination unit 230 includes an optical system that emits in a direction toward a subject illumination light that is emitted from the light source apparatus 350 and is guided by an optical fiber.

An image of the subject illuminated by the illumination light emitted from the illumination unit 230 is in focus on the imaging plane of the each imaging device of the imaging unit 210 via the imaging optical system 220. The imaging unit 210 generates image data based on the subject image by an imaging operation. The image data contains a left image that is generated by the left image acquisition unit 211 and a right image that is generated by the right image acquisition unit 212. The image data is transmitted to the image processing apparatus 100 via the cable.

The image processing apparatus 100 includes an image acquisition circuit 110, an image memory 120, an interference area setting circuit 130, an interference area corrector 140, and a display image generator 150.

The image acquisition circuit 110 acquires the image data from the endoscope 200. The image memory 120 divides the image data acquired by the image acquisition circuit 110 into left image data and right image data and stores both the image data. For example, the image memory 120 includes a semiconductor memory such as a DRAM. Various processes are performed by using the image stored in the image memory 120.

The interference area setting circuit 130 sets an interference area in each of the left image data and the right image data stored in the image memory 120. Here, the interference area is an image area that gives discomfort to a user in observation. The interference area setting circuit 130 functions as an interference candidate area extractor 131, a labeling circuit 132, and an interference area selector 133. The interference candidate area extractor 131 extracts a candidate of the interference area as an interference candidate area based on a characteristic of the image acquired from the image memory 120. The labeling circuit 132 labels each of one or a plurality of extracted interference candidate areas. The interference area selector 133 removes an area such as a bright spot other than the interference area from the labeled interference candidate areas acquired from the labeling circuit 132, based on the characteristic of the image acquired from the image memory 120, and selects an interference area.

The interference area corrector 140 acquires the image from the image memory 120, acquires data of the interference area from the interference area selector 133, and performs correction on the set interference area in the image. The correction is an image process for reducing the discomfort of the user with the interference area. For example, the correction can include a process of reducing luminance of the interference area. The display image generator 150 performs another image process on image data corrected by the interference area corrector 140. The image process includes various processes for making the image suitable for a display on the display 300 and also includes an image process for displaying a three-dimensional image, for example. The displaying image data processed by the display image generator 150 is output to the display 300.

For example, the interference area setting circuit 130, the interference area corrector 140, the display image generator 150, and the like include an integrated circuit or the like such as an application specific integrated circuit (ASIC), a field programmable gate array (FPGA), a graphics processing unit (GPU), or a central processing unit (CPU). The interference area setting circuit 130, the interference area corrector 140, the display image generator 150, and the like may be each configured of one integrated circuit or the like or may be each configured of a combination of a plurality of integrated circuits. In addition, two or more of the interference area setting circuit 130, the interference area corrector 140, the display image generator 150, and the like may be each configured of one integrated circuit or the like. The integrated circuits operate in accordance with a program recorded in a recording device (not illustrated) provided in the image processing apparatus 100 or recorded in a recording area in the integrated circuit.

The display 300 is a 3D display. The display 300 displays a three-dimensional image, based on the displaying image data acquired from the image processing apparatus 100. For example, the display 300 is the 3D display using polarized light. In this case, the user wears polarized glasses to see the image displayed on the display 300, thereby, being able to recognize the displayed image as the three-dimensional image.

<Mode of Use of Endoscope System>

A mode of use of the endoscope system 1 is described. FIG. 2 is a schematic view illustrating an example of a state of a procedure using the endoscope system 1. An insertion part 240 of the endoscope 200 is inserted into an inside of a subject 420. As illustrated in FIG. 2, a distal portion of the insertion part 240 has the left optical system 221 and the right optical system 222 of the imaging optical system 220. The three-dimensional image is displayed on the display 300, based on the left image and the right image that are acquired via the two optical systems. In addition, the distal portion of the insertion part 240 has the illumination unit 230. Two illumination windows, through which the illumination light is emitted, are drawn on the illumination unit 230 in FIG. 2; however, one or three or more illumination windows may be provided. In addition, the left optical system 221, the right optical system 222, and the illumination unit 230 may have any positional relationship or the like. For example, the illumination windows of the illumination unit 230 may be arranged in a ring shape so as to surround the left optical system 221 and the right optical system 222.

In addition to the insertion part 240 of the endoscope 200, forceps 410 or the like is inserted into the inside of the subject 420, and a procedure is performed on tissue 422 which is a procedure target. One pair of forceps 410 is drawn in FIG. 2; however, a plurality of pairs of forceps may be inserted into the subject 420, or a procedure tool that performs a procedure on the tissue 422 by using high-frequency electric power, ultrasonic vibration, heat energy, or the like may be inserted into the inside of the subject 420. While the user views the image that is acquired by the endoscope 200 and displayed on the display 300, the user performs the procedure on the tissue 422 which is the procedure target by using the forceps 410 or the like.

<Operation of Image Processing Apparatus>

An image processing that is performed by the image processing apparatus is described with reference to a flowchart illustrated in FIG. 3.

In Step S101, the image acquisition circuit 110 acquires the image data obtained by imaging from the imaging unit 210 of the endoscope 200. Here, the acquired image data contains left image data obtained by the left image acquisition unit 211 and right image data obtained by the right image acquisition unit 212. In Step S102, the image memory 120 temporarily stores the acquired image data. In this case, the left image data and the right image data are separately stored.

In Step S103, the interference area setting circuit 130 selects an image on which the following processes are to be performed. Specifically, the interference area setting circuit 130 selects one from the left image data and the right image data.

Figure 4:
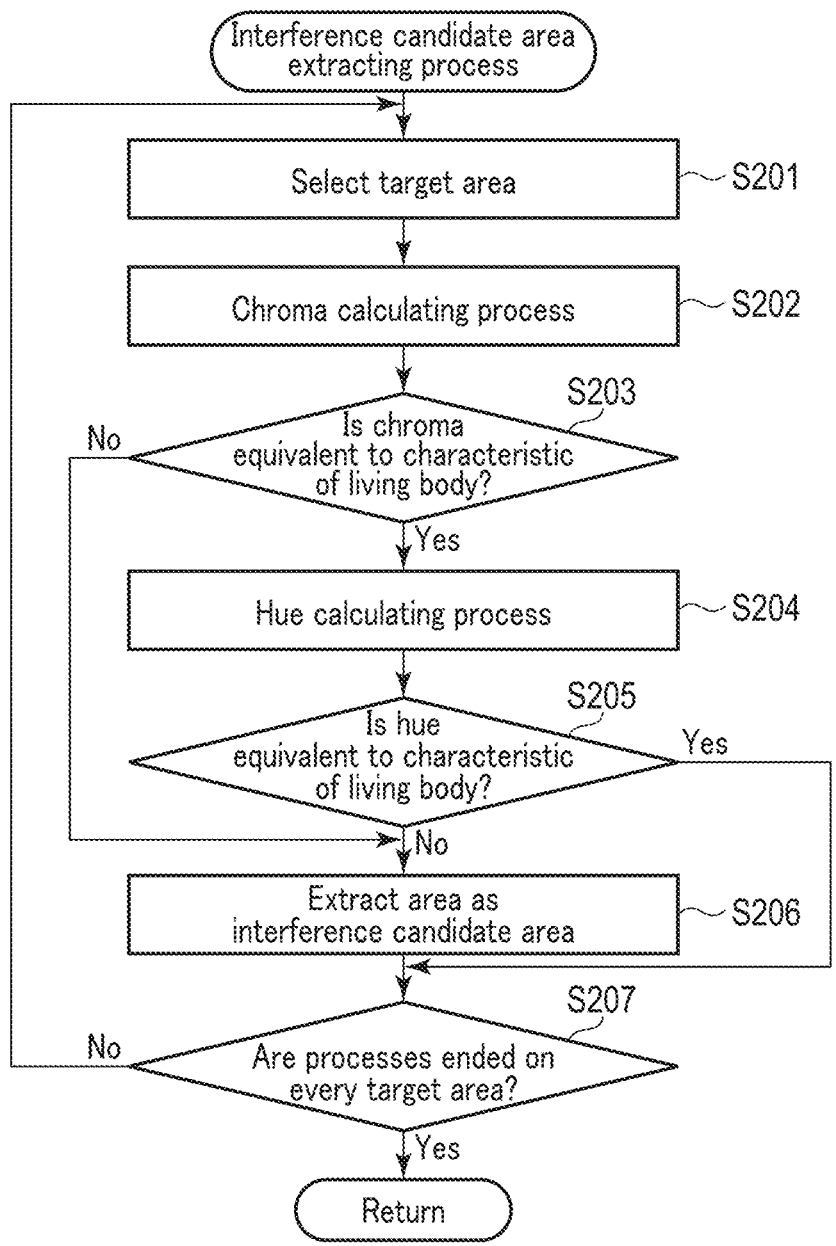
FIG. 4 is a flowchart schematically illustrating an example of an interference candidate area extracting process according to the embodiments.

In Step S104, the interference candidate area extractor 131 performs an interference candidate area extracting process. In the interference candidate area extracting process, the interference candidate area extractor 131 extracts, as an interference candidate area, an area other than a region having the characteristic of the image such as a characteristic of a color of a living body, in the image data stored in the image memory 120. For example, the interference candidate area extractor 131 extracts the interference candidate area by using the characteristic related to color such as chroma information or hue information of the image. An example of the interference candidate area extracting process is described with reference to FIG. 4.

In Step S201, the interference candidate area extractor 131 selects an area which becomes a target of processes of subsequent Step S202 to Step S207. The selected area is a rectangular area having one or more pixels, for example. Incidentally, the selected area may not have a rectangular shape. In Step S202, the interference candidate area extractor 131 calculates chroma of the area which is a target selected in Step S201. For example, the interference candidate area extractor 131 converts RGB signals into YCbCr signals and calculates the chroma. Of the YCbCr signals, the Cb signal and Cr signal are normalized into the Y signal. In this manner, a reflection intensity of the subject is $$\text{Sat} = (\Sigma_{y=1}^{SizeY} \Sigma_{x=1}^{SizeX} \text{NormCb}(x,y))^2 + (\Sigma_{y=1}^{SizeY} \Sigma_{x=1}^{SizeX} \text{NormCr}(x,y))^2 \quad (1)$$

removed, and only the characteristic of the color can be handled. For example, a characteristic value of the chroma can be calculated, based on a distance from an origin to a point indicated by a Cb signal value and a Cr signal value normalized by the Y signal in a space with axes of Cb and Cr normalized by the Y signal. Specifically, the feature value of the chroma can be calculated from the following Equation (1), for example: Here, Sat represents chroma within an area, x and y represent a pixel position, SizeX and SizeY represent a size of the area set in Step S201, NormCb and NormCr represent a Cb signal value and a Cr signal value normalized by the Y signal.

Incidentally, an example in which a YCbCr space is used in the calculation of chroma is described here; however, an HLS space or the like may be used.

In Step S203, the interference candidate area extractor 131 determines whether or not the chroma calculated in Step S202 is equivalent to the characteristic of the living body. Here, a characteristic of a living body for comparison may be set in advance. For example, when the chroma is a value of an achromatic color or is approximate thereto, the chroma is determined not to be equivalent to the characteristic of the living body. When the chroma is not equivalent to the characteristic of the living body, the process proceeds to Step S206 to be described below. On the one hand, when the chroma is equivalent to the characteristic of the living body, the process proceeds to Step S204.

In Step S204, the interference candidate area extractor 131 calculates hue of the area which is the target. Similarly to the calculation of the chroma, the calculation of the hue may be performed by using the Cb signal value and the Cr signal value normalized by the Y signal. For example, a characteristic value of the hue can be calculated, based on an angle of the point indicated by the Cb signal value and the Cr signal value normalized by the Y signal in a space with axes of Cb and Cr normalized by the Y signal. Specifically, the feature value of the hue can be calculated from the following $$H = \arctan(\Sigma_{y=1}^{SizeY}\Sigma_{x=1}^{SizeX} \text{Norm}Cb(x,y), \Sigma_{y=1}^{SizeY}\Sigma_{x=1}^{SizeX} \text{Norm}Cr(x,y)) \quad (2)$$

Equation (2), for example:
Here, H represents hue, and arctan(a, b) represents an arctangent value of a and b. Instead of arctangent, a sign and a slope in a Cb and Cr space normalized by the Y signal may be calculated.

Incidentally, an example in which a YCbCr space is used in the calculation of hue is described here; however, the HLS space or the like may be used.

In Step S205, the interference candidate area extractor 131 determines whether or not the hue calculated in Step S204 is equivalent to the characteristic of the living body. A characteristic of a living body for comparison may be set in advance. For example, when the hue is reddish, the hue is determined to be equivalent to the characteristic of the living body. When the hue is not equivalent to the characteristic of the living body, the process proceeds to Step S206. On the one hand, when the hue is equivalent to the characteristic of the living body, the process proceeds to Step S207.

In Step S206, the interference candidate area extractor 131 extracts the area as an interference candidate area. Then, the process proceeds to Step S207. As described above, when the chroma is not equivalent to the characteristic of the living body or when the chroma is equivalent to the characteristic of the living body but the hue is not equivalent to the characteristic of the living body, the area is extracted as the interference candidate area. Otherwise, the area is not extracted as the interference candidate area.

In Step S207, the interference candidate area extractor 131 determines whether or not every area in the image is processed as the target area. When every area is not processed as the target area, the process returns to Step S201. On the one hand, when every area is processed as the target area, the interference candidate area extracting process is ended, and the process returns to the image process.

The interference candidate area extracting process is described with reference to a schematic view. For example, a case where an image 710 as illustrated in FIG. 5 is acquired by the endoscope 200 is considered. In the image 710 illustrated in FIG. 5, an internal organ 711 which is the living body and forceps 712 are shown. In general, the forceps 712 have a color characteristic different from that of the internal organ 711 or the like which is an observation target. In addition, a region of the forceps 712 close to the imaging unit 210 of the endoscope 200 has higher luminance than another portion thereof. In addition, in the image 710, the living body such as the internal organ 711 other than the forceps 712 has a bright spots 716. The bright spot 716 has RGB signal values that are each approximate to a saturation value, and thus the chroma that is calculated in the process of Step S202 can be a value of an achromatic color or can be approximate thereto. In this case, the bright spot 716 has the chroma that is not equivalent to the characteristic of the living body and can be extracted as the interference candidate area. In addition, even when the chroma calculated in the process of Step S202 is determined to be equivalent to the characteristic of the living body, the hue of the bright spot 716 is different from that of the internal organ 711 or the like in some cases. In this case, the bright spot 716 has the hue that is not equivalent to the characteristic of the living body and can be extracted as the interference candidate area. As described above, when the above-described interference candidate area extracting process is performed on the image 710, for example, the forceps 712, the bright spots 716, and the like can be extracted as the interference candidate area.

FIG. 6 illustrates a schematic view of extracted interference candidate area data 720. In FIG. 6, white areas represent the extracted interference candidate areas. That is, the interference candidate area data 720 contains information indicating a first area 722 corresponding to the forceps 712 and second areas 726 corresponding to the bright spots 716.

Incidentally, an example in which the interference candidate area is extracted by using the chroma information and the hue information is provided; however, the invention is not limited thereto. The interference candidate area may be extracted by using one of the chroma information and the hue information. In addition, the interference candidate area may be extracted by using a characteristic related to color other than the chroma information or the hue information. In addition, the interference candidate area may be extracted by using a characteristic of the image other than the color, the characteristic indicating a different value between the observation target and the interference area.

Figure 3:
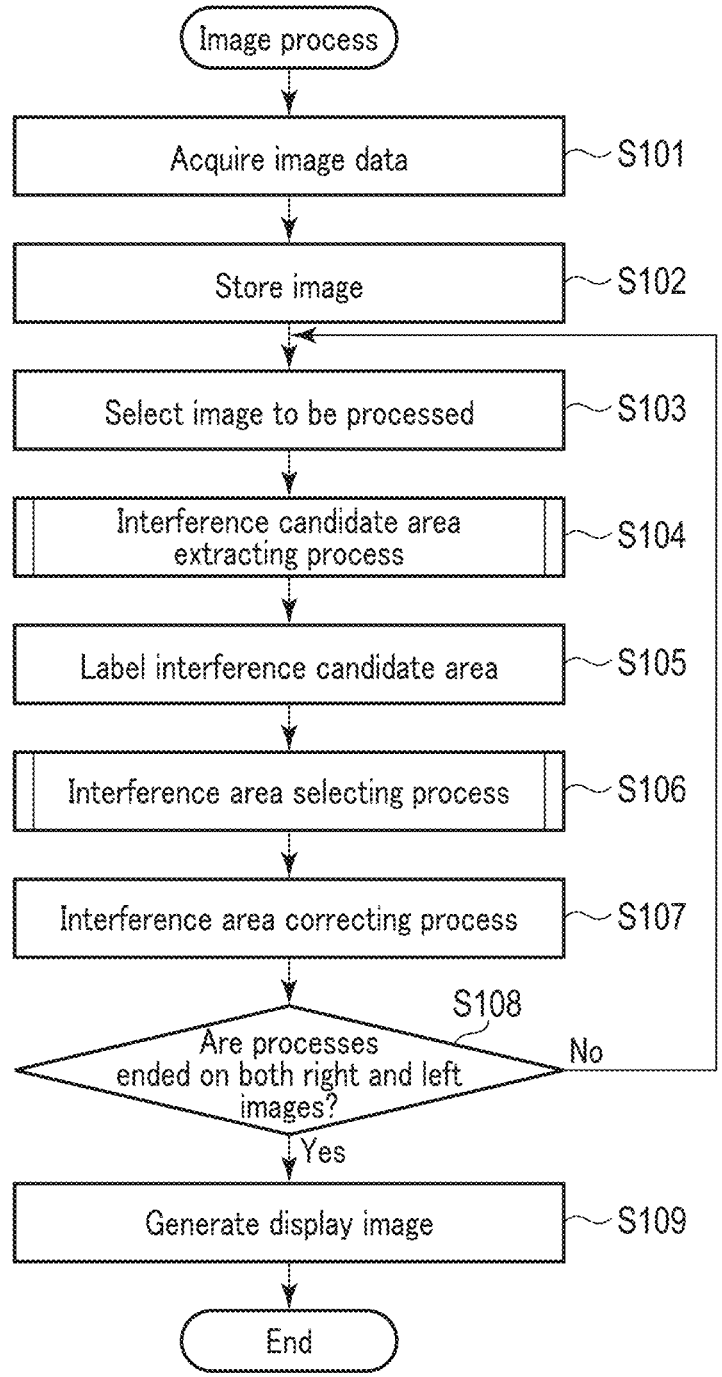
FIG. 3 is a flowchart schematically illustrating an example of an image process performed by an image processing apparatus according to the embodiments.

The description back to FIG. 3 is continued. In the embodiment, correction for reducing luminance in the first area 722 corresponding to the forceps 712 is performed, and correction is not performed on the second area 726 corresponding to the bright spot 716. Therefore, it is necessary to distinguish between the first area 722 and the second area 726 in the subsequent process.

In Step S105, the labeling circuit 132 executes a labeling process of labeling the interference candidate areas extracted in the interference candidate area extracting process. In the labeling process, the labeling circuit 132 first sets areas having one or more pixels in order. When the set area is the interference candidate area, and a labeled area is not present in eight adjacent areas around the area, the set area is labeled with new number. When the set area is the interference candidate area, and a labeled area is present in eight adjacent areas around the area, the set area is labeled with the same number as a label present in advance. An area other than the interference candidate area is not labeled. Such a method described here is an example of the labeling process, and labeling may be performed by any other method including various methods which are generally used.

Figure 7:
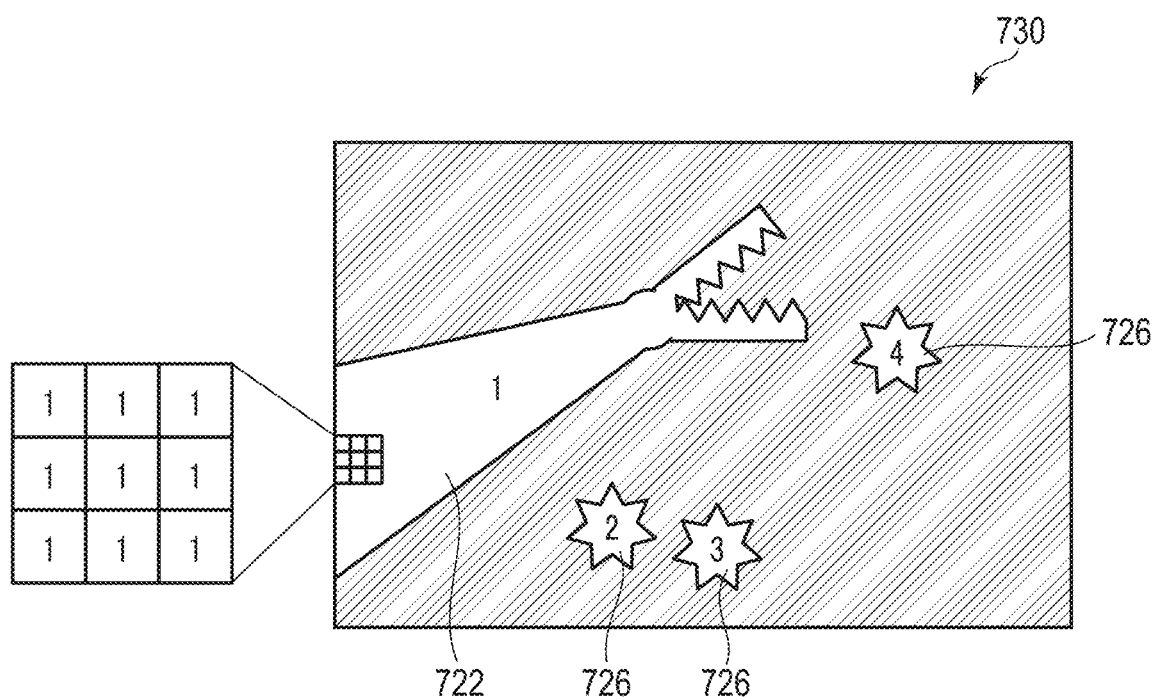
FIG. 7 is a view for describing the image process according to the embodiments, that is, a schematic view illustrating labeled interference candidate areas.

As an example, FIG. 7 illustrates a result of the labeling process performed on the interference candidate area data illustrated in FIG. 6. As illustrated in FIG. 7, in labeling data 730, a label "1" is assigned to the first area 722 corresponding to the forceps 712, and labels "2", "3", and "4" are assigned to the second areas 726 corresponding to the bright spots 716.

Figure 8:
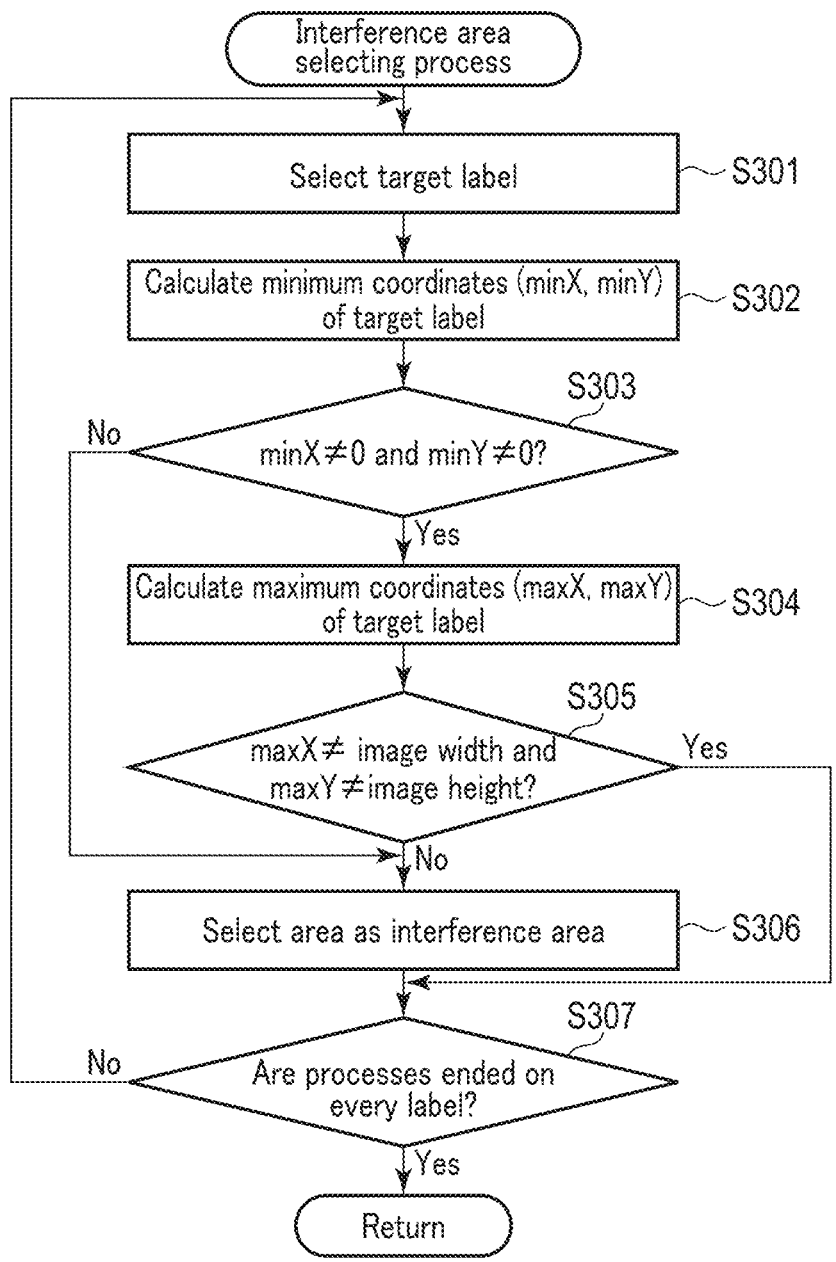
FIG. 8 is a flowchart schematically illustrating an example of an interference area selecting process according to a first embodiment.

In Step S106, the interference area selector 133 performs an interference area selecting process of selecting an interference area, based on the image data stored in the image memory 120 and labeling data processed by the labeling circuit 132. As illustrated in FIG. 2, in general, the procedure tool such as the forceps 410 is inserted toward the tissue 422 from an outer side of an angle of view in the imaging optical system 220 of the insertion part 240 of the endoscope 200. Therefore, in FIG. 5, the forceps 712 are closest to the imaging optical system 220 of the endoscope 200 at an image end, and thus there is a high possibility that it is not possible to achieve a stereoscopic view. In addition, the forceps 712 have high luminance because the forceps 712 are closest to the illumination unit 230 at the image end, and thus the forceps 712 are likely to catch an eye. In the embodiment, an area extended from a peripheral edge of the image 710 toward an inside of the image 710 is set as the interference area from the interference candidate areas such that an area such as the forceps 712 which is close to the endoscope 200 is extracted as the interference area. That is, the interference area is selected, based on positional information related to the interference candidate area. The interference area selecting process is described with reference to FIG. 8.

In Step S301, the interference area selector 133 selects a label which becomes a target of processes of Step S302 to Step S306. For example, in an example illustrated in FIG. 7, labels 1 to 4 are selected in order.

In Step S302, the interference area selector 133 determines a minimum value minX of an x coordinate and a minimum value minY of a y coordinate from pixels within an area with the label which is the target. For example, minX represents the leftmost pixel in the area with the corresponding label in the image. For example, minY represents the uppermost pixel in the area with the corresponding label in the image.

In Step S303, the interference area selector 133 determines whether or not minX≠0 and minY≠0. When minX is 0, this indicates that the area with the corresponding label is in contact with a left end of the image 710. When minY is 0, this indicates that the area with the corresponding label is in contact with an upper end of the image 710. When minX=0 or minY=0, the process proceeds to Step S306 to be described below. On the one hand, when minX≠0 and minY≠0, the process proceeds to Step S304.

In Step S304, the interference area selector 133 determines a maximum value maxX of the x coordinate and a maximum value maxY of the y coordinate from the pixels within the area with the label which is the target. For example, maxX represents the rightmost pixel in the area with the corresponding label in the image. For example, maxY represents the lowermost pixel in the area with the corresponding label in the image.

In Step S305, the interference area selector 133 determines whether or not maxX≠width of image 710 and minY≠height of image 710. When maxX is the width of the image 710, this indicates that the area with the corresponding label is in contact with a right end of the image 710. When maxY is the height of the image 710, this indicates that the area with the corresponding label is in contact with a lower end of the image 710. When maxX=width of image 710 or maxY=height of image 710, the process proceeds to Step S306. On the one hand, when maxX≠width of image 710 or minY≠height of image 710, the process proceeds to Step S307.

In Step S306, the interference area selector 133 selects, as an interference area, the interference candidate area related to the corresponding label. That is, when the interference candidate area is in contact with an end portion or a side of the image 710, the area is selected as the interference area. Then, the process proceeds to Step S307.

In Step S307, the interference area selector 133 determines whether or not the processes described above are ended regarding every label. When the processes are not ended on every label, the process returns to Step S301. On the one hand, when the processes are ended on every label, the interference area selecting process is ended, and the process returns to the image process.

Figure 9:
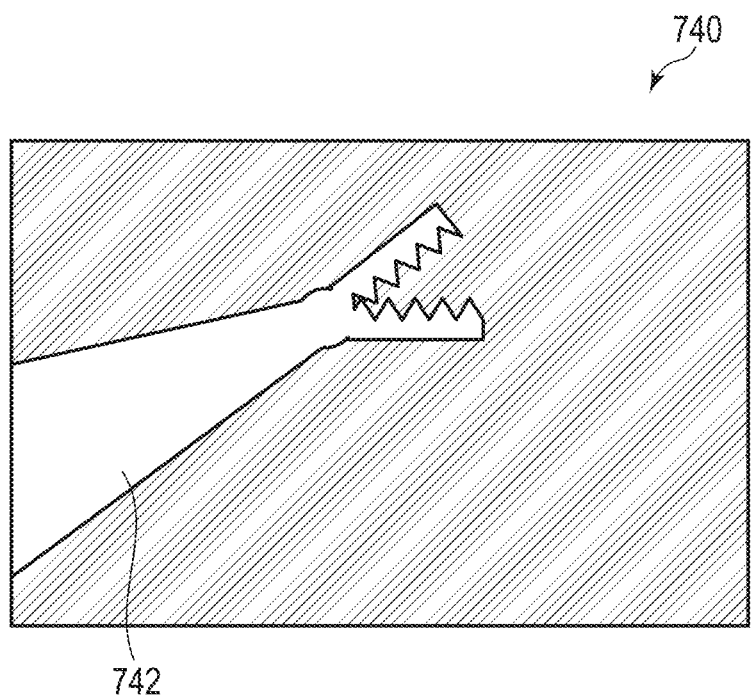
FIG. 9 is a view for describing the image process according to the embodiments, that is, a schematic view illustrating a selected interference area.

FIG. 9 illustrates a schematic view of interference area data generated in the interference area selecting process. Only an area 742 corresponding to the forceps 712 is selected in interference area data 740.

The description back to FIG. 3 is continued. In Step S107, the interference area corrector 140 performs an interference area correcting process. That is, the interference area corrector 140 acquires data of an image as a process target from the image memory 120 and acquires interference area data indicating the interference area from the interference area selector 133. The interference area corrector 140 determines a pixel corresponding to the interference area in the image and performs a correcting process of reducing a luminance value of the image on the corresponding pixel.

A reduction in luminance value may be stored in a table or the like or may be calculated depending on the luminance value. For example, it is preferable to reduce the luminance to two thirds of a maximum value of the luminance of a pixel in the interference area. For example, adjustment of the luminance value may be performed by γ correction.

When the luminance value is reduced in the interference area by the correcting process, a color may be intensely perceived in a case or the like where a living body is reflected in the forceps 712, for example. Hence, a correcting process of reducing chroma proportional to a reduction in the luminance value may also be performed on a pixel related to the interference area, for example. As described above, the correcting process of making the interference area inconspicuous in the image is performed. As a result, an interference feeling occurring when viewing the image is reduced in a processed image.

In Step S108, the image processing apparatus 100 determines whether or not the left image and the right image stored in the image memory 120 are both processed. When both images are processed, the process proceeds to Step S109. Otherwise, the process returns to Step S103.

In Step S109, the display image generator 150 acquires image data subjected to the correcting process, performs another image process for display including an image process for the three-dimensional display, and generates a display image. The display image generator 150 outputs data of the generated display image to the display 300 and causes the display 300 to display the display image.

Figure 10A:
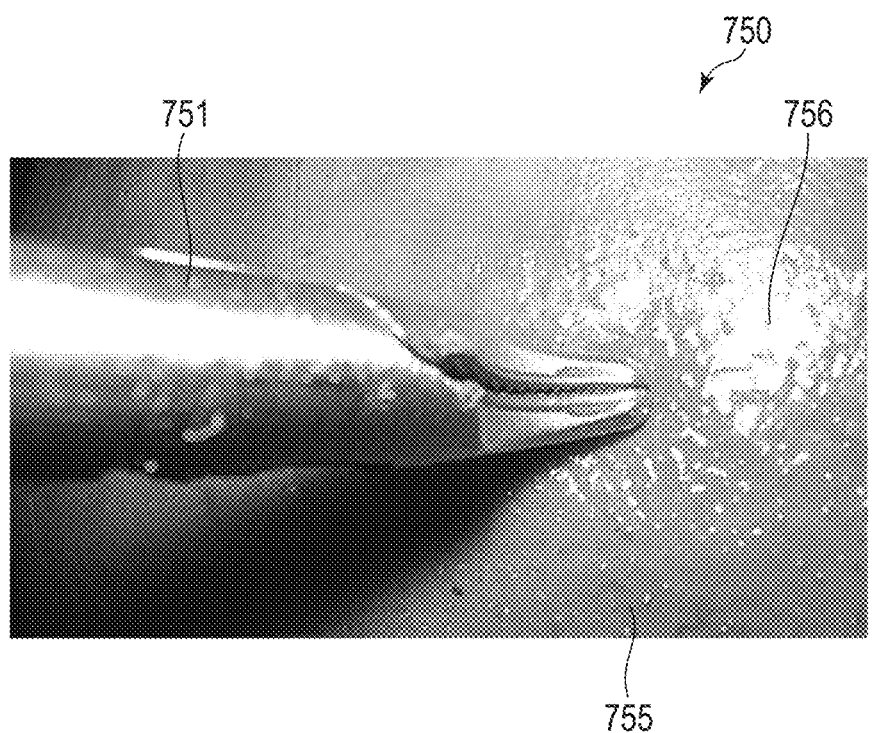
FIG. 10A is a view for describing the image process according to the embodiments, that is, an example of an image before a correcting process.
Figure 10B:
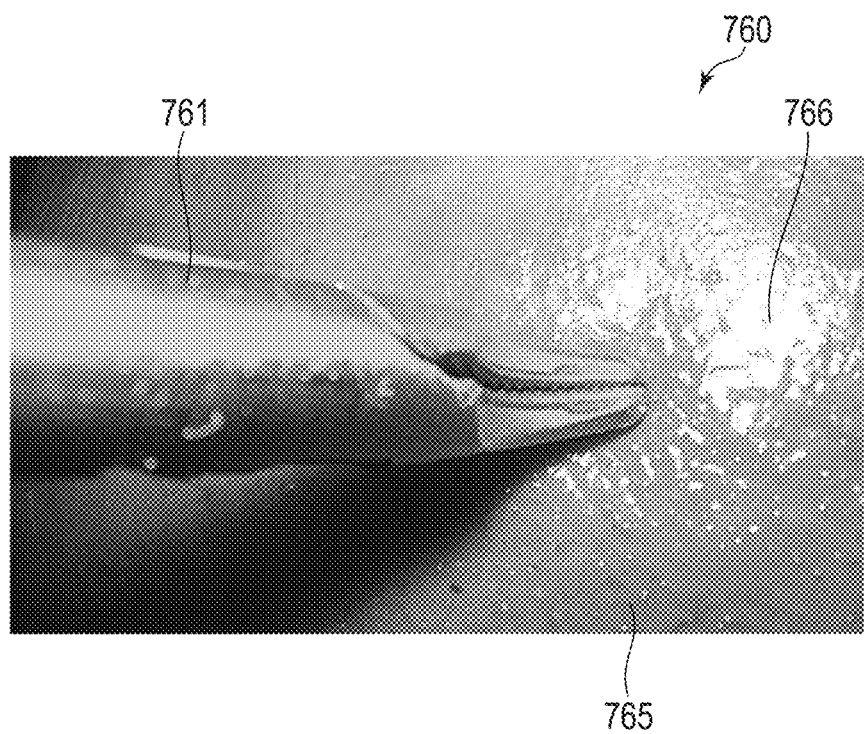
FIG. 10B is a view for describing the image process according to the embodiments, that is, an example of the image after the correcting process.

FIG. 10A illustrates an example of a first image 750 when the image process according to the embodiment is not performed, and FIG. 10B illustrates an example of a second image 760 when the image process is performed. Halation occurs in forceps 751 in the first image 750 illustrated in FIG. 10A. By comparison, luminance of forceps 761 is reduced in the second image 760 illustrated in FIG. 10B. On the one hand, in the first image 750, a bright spot 756 shown in a living body 755 remains as a bright spot 766 shown in a living body 765 also in the second image 760.

<Feature of Endoscope System>

In the endoscope system 1 according to the embodiment, the luminance of the interference area such as a high-luminance area of a procedure tool such as forceps that enters from an outside of a screen is reduced, for example. As a result, the discomfort felt by the user is reduced.

MODIFICATION EXAMPLES

Figure 11A:
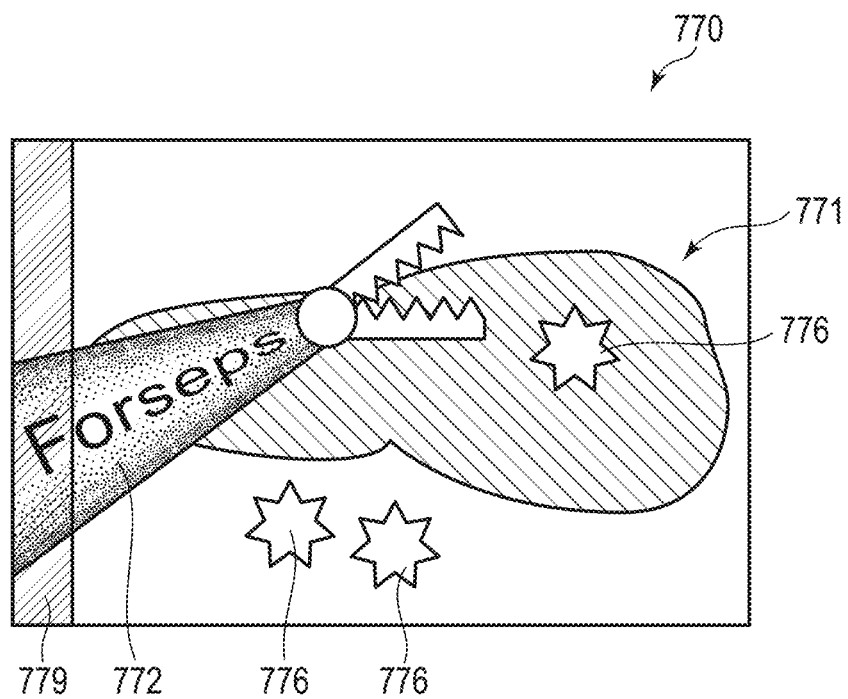
FIG. 11A is a view for describing a non-corresponding area, that is, a schematic view illustrating a left image.
Figure 11B:
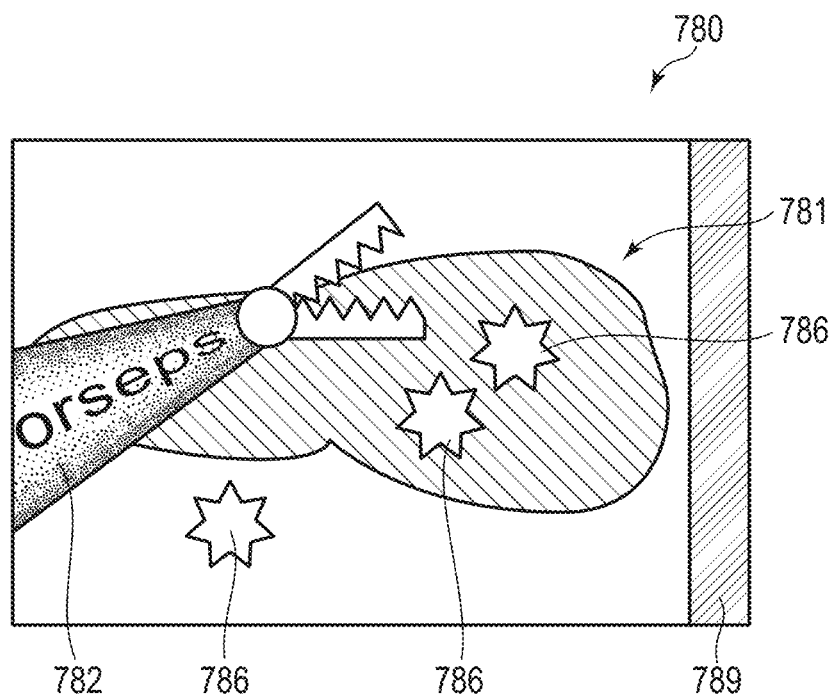
FIG. 11B is a view for describing a non-corresponding area, that is, a schematic view illustrating a right image.

FIG. 11A illustrates a schematic view of a left image 770, and FIG. 11B illustrates a schematic view of a right image 780. In general, a visual field is different between a pair of left image 770 and right image 780. Therefore, the left image 770 contains a first non-corresponding area 779 that is captured in the left image 770 but is not captured in the right image 780. Similarly, the right image 780 contains a second non-corresponding area 789 that is captured in the right image 780 but is not captured in the left image 770.

The first non-corresponding area 779 and the second non-corresponding area 789 are areas that cannot be seen in the stereoscopic view. When the first non-corresponding area 779 and the second non-corresponding area 789 are conspicuous, a user feels discomfort. Hence, the interference area setting circuit 130 may set the first non-corresponding area 779 and the second non-corresponding area 789 as the interference area, in addition to the interference area according to the embodiment described above or instead of the interference area according to the embodiment described above. That is, the interference area setting circuit 130 may set, on an image, an interference area including the area captured only by one image of a pair of images captured by using a three-dimensional endoscope. As a result, the interference area corrector 140 performs, on the first non-corresponding area 779 and the second non-corresponding area 789, the same image process as the image process that is performed on the interference area in the embodiment described above. In this manner, a line of vision of a user is unlikely to be directed to the non-corresponding area, and the discomfort felt by the user is reduced.

In addition, the interference area setting circuit 130 may set, as an interference area, from a range of the interference area as selected in the embodiment described above, a range being contained in the non-corresponding area, and the interference area corrector 140 may perform correction on the corresponding area.

In addition, in the embodiment described above, an example in which the entire forceps 712 are set as the interference area; however, the invention is not limited thereto. For example, the interference area setting circuit 130 may set, as the interference area, an area of the forceps 712 having a luminance value higher than a predetermined value.

As described above, the interference area in the embodiment described above is described as an example, and the interference area can be various areas that give discomfort or the like to a user.

Second Embodiment

Figure 12A:
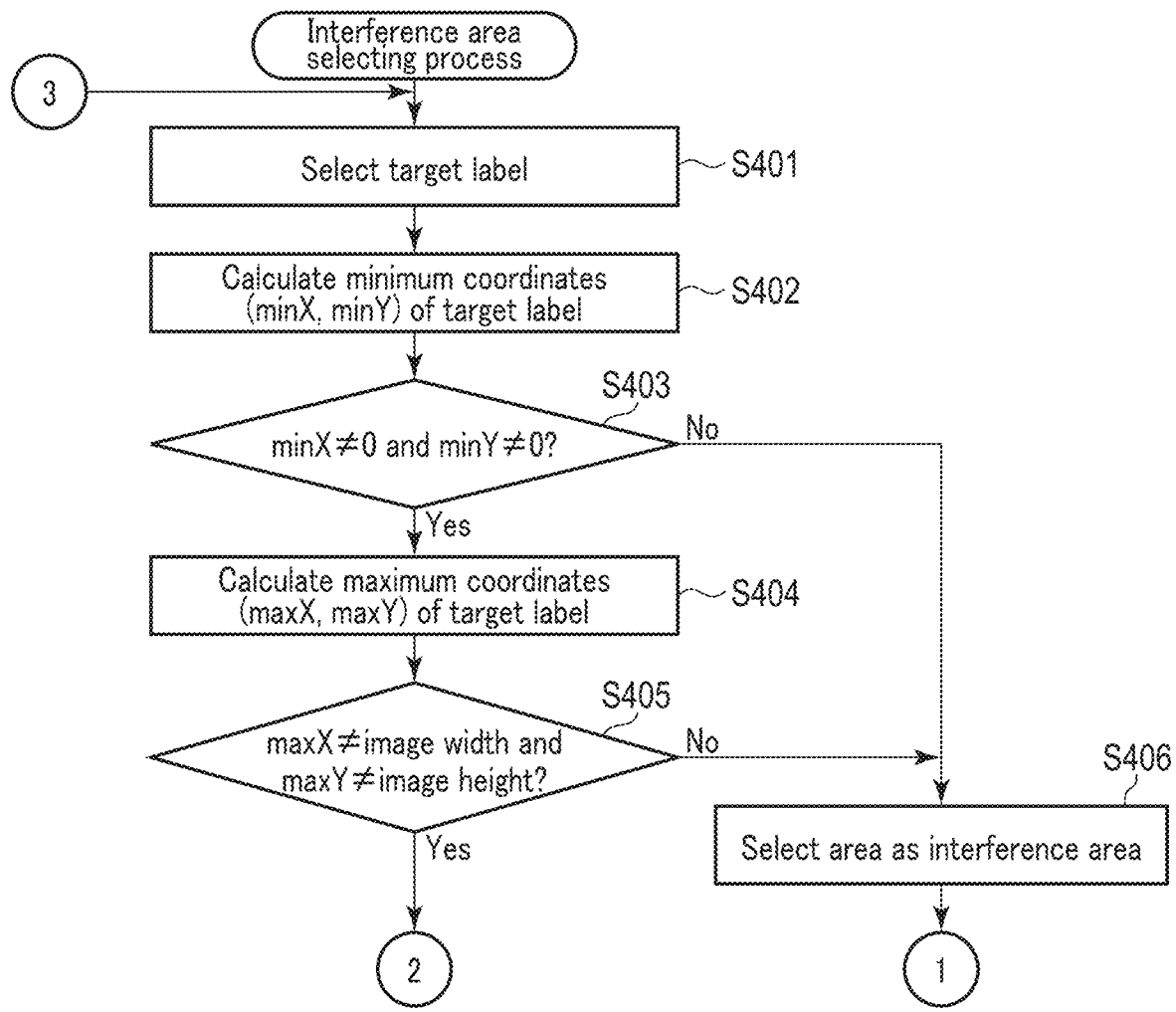
FIG. 12A is a flowchart schematically illustrating an example of an interference area selecting process according to a second embodiment.
Figure 12B:
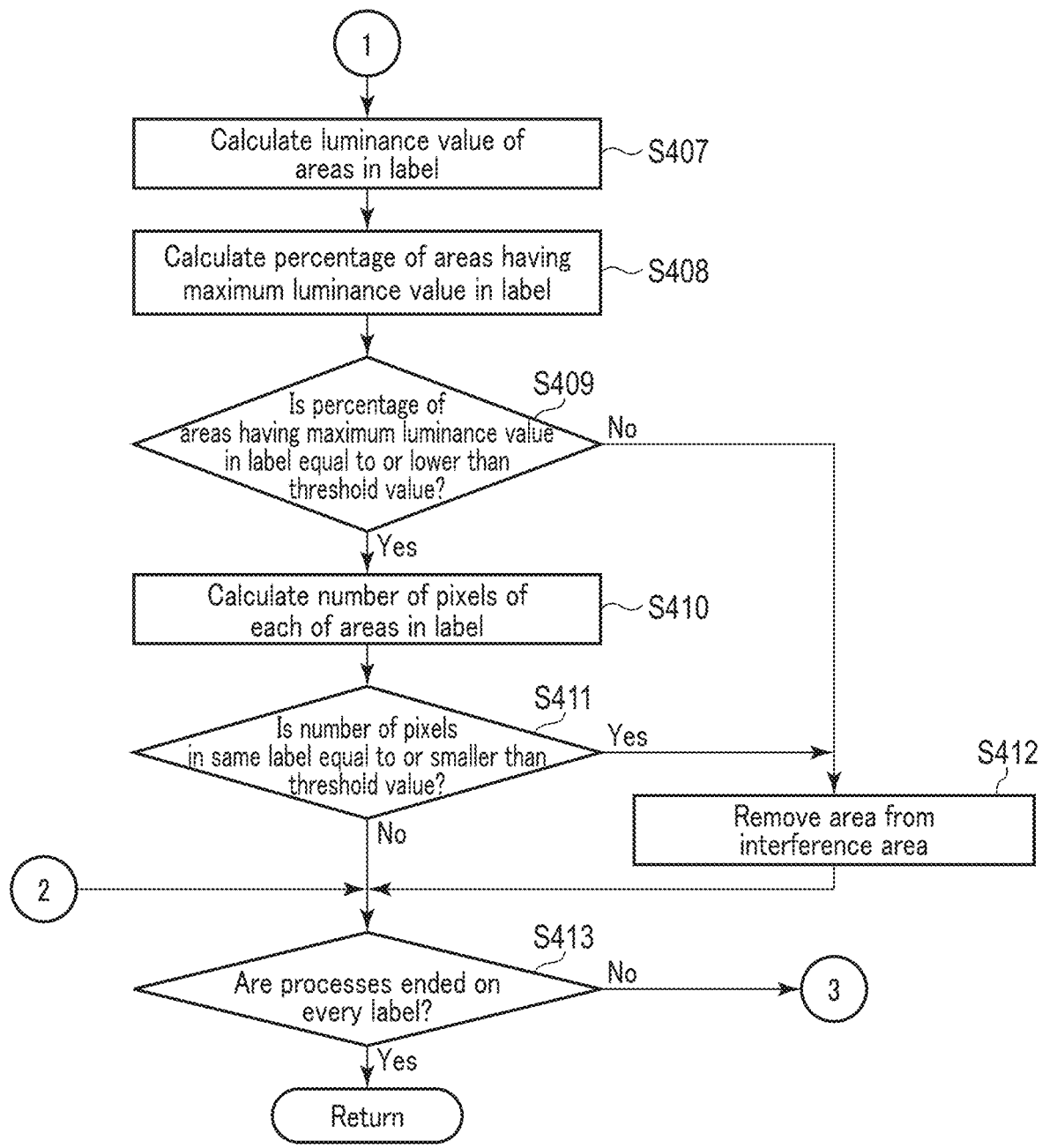
FIG. 12B is a flowchart schematically illustrating an example of the interference area selecting process according to the second embodiment.

The second embodiment is described. Here, differences from the first embodiment are described, and the same reference signs are assigned to the same portions, and thereby the description thereof is omitted. In the first embodiment, the interference area is determined, based on the fact that the interference area is in contact with the end portion or the side of the image 710. However, in this method, there is a concern that, when the bright spot 716 is present in contact with the end portion of the image 710, the bright spot 716 is extracted as the interference area. Hence, in the embodiment, the interference area is determined as follows, such that an area of the procedure tool is more stably selected. That is, the procedure tool often has a cylindrical handle, in general, and thus the luminance is distributed in a broad range in the handle of the procedure tool. On the one hand, a significant bias in distribution of the luminance occurs in the bright spot of the living body. In the embodiment, the interference area is determined by using luminance distribution in a label and a size of the label. The interference area selecting process according to the embodiment is described with reference to a flowchart illustrated in FIGS. 12A and 12B.

In the interference area selecting process according to the embodiment, processes of Step S401 to Step S406 are the same as those of Step S301 to Step S306 in the interference area selecting process according to the first embodiment. To put it briefly, In Step S401, the interference area selector 133 selects a label which becomes a target of the subsequent processes. In Step S402, the interference area selector 133 determines a minimum value minX of the x coordinate and a minimum value minY of the y coordinate from pixels within an area with the label which is the target. In Step S403, the interference area selector 133 determines whether or not minX$\neq$0 and minY$\neq$0. When minX=0 or minY=0, the process proceeds to Step S406 to be described below. On the one hand, when minX$\neq$0 and minY$\neq$0, the process proceeds to Step S404. In Step S404, the interference area selector 133 determines a maximum value maxX of the x coordinate and a maximum value maxY of the y coordinate from the pixels within the area with the label which is the target. In Step S405, the interference area selector 133 determines whether or not maxX$\neq$width of image 710 and minY$\neq$height of image 710. When maxX=width of image 710 or maxY=height of image 710, the process proceeds to Step S406. On the one hand, when maxX$\neq$width of image 710 or minY$\neq$height of image 710, the process proceeds to Step S413. In Step S406, the interference area selector 133 selects, as an interference area, an interference candidate area related to the corresponding label. Then, the process proceeds to Step S407. That is, when the interference candidate area is in contact with an end of the image 710, the corresponding area is selected as the interference area, and the process proceeds to Step S407.

Processes of Step S407 to Step 409 are processes of extracting an area indicating a bright spot 716 of the living body by using the luminance distribution in the label. Many areas having a saturated luminance value are present in areas of the bright spot 716 extracted as the interference candidate area. On the one hand, the procedure tool often has a cylindrical handle, in general, and thus distribution of luminance value is wide. Hence, the distribution of the luminance value is focused, and the bright spot 716 of the living body is removed from the interference area.

In Step S407, the interference area selector 133 calculates a luminance value in each of the areas in the label. Here, the areas are rectangular areas having one or more pixels, for example. Incidentally, the area may not have a rectangular shape. In addition, the luminance value may be a luminance signal value that is generated based on the RGB signals, for example.

In Step S408, the interference area selector 133 calculates an occupation percentage of areas having a maximum luminance value in the label. Here, the occupation percentage of the areas having the maximum luminance value in the label is a value obtained by dividing the number of areas having the maximum luminance value or luminance values within a predetermined range, compared with the maximum luminance value, by the number of areas, in the label. Instead of the occupation percentage of the areas having the maximum luminance value or the luminance values within the predetermined range, compared with the maximum luminance value, in the label, an occupation percentage of areas having a saturation value of the luminance or luminance values within a predetermined range, compared with the saturation value, in the label, may be used. In addition, an occupation percentage of areas having another predetermined luminance value in the label may be used. For example, a predetermined threshold value may be determined based on a histogram of the luminance, and an occupation percentage of areas having luminance equal to or higher than the threshold value in the label may be used.

In Step S409, the interference area selector 133 performs threshold value determination on the calculated occupation percentage of areas having the maximum luminance value in the label. That is, the interference area selector 133 determines whether or not the percentage is equal to or lower than the predetermined threshold value. The threshold value used here is not limited thereto and is preferably about 70%, for example. When the percentage of the areas having the maximum luminance value in the label is higher than the threshold value, the process proceeds to Step S412, and the corresponding areas are removed from the interference area. On the one hand, when the percentage is equal to or lower than the threshold value, the process proceeds to Step S410.

Processes of Step S410 and Step S411 are processes of extracting an area indicating the bright spot 716 of the living body by using a size of the label. The bright spot 716 extracted as the interference candidate area includes a very small bright spot. In the very small bright spot 716, the percentage of the area having the maximum luminance value in the label is low, and thus the bright spot 716 of the living body is not accurately selected based on the luminance distribution. Hence, the size of the label is focused, and the very small bright spot 716 of the living body is removed from the interference area.

In Step S410, the interference area selector 133 calculates the number of pixels in the same label. In Step S411, the interference area selector 133 determines whether or not the number of pixels in the same label is equal to or smaller than a predetermined threshold value. Here, the threshold value is not limited thereto, for example, and may be about 100 pixels with respect to a hi-vision image. When the number of pixels in the same label is equal to or smaller than the predetermined threshold value, the process proceeds to Step S412. In Step S412, the interference area selector 133 removes, from the interference area, areas of the label determined as the bright spot 716 in the determination described above from a target selected as the interference area and determines that the corresponding area is not the interference area. Then, the process proceeds to Step S413.

When the number of pixels is determined to be not equal to or smaller than the threshold value in Step S411, the process proceeds to Step S413. That is, a label that is selected as the interference area and is set as a target is not removed from the interference area and is determined to be the interference area.

In Step S413, the interference area selector 133 determines whether or not the processes described above are ended regarding every label. When the processes are not ended on every label, the process returns to Step S401. On the one hand, when the processes are ended on every label, the interference area selecting process is ended, and the process returns to the image process.

In the interference area selecting process according to the embodiment, the interference area can be selected with higher accuracy, compared with the interference area selecting process according to the first embodiment.

Incidentally, it is needless to say that the embodiment can be used to be combined with the modification examples described above.

MODIFICATION EXAMPLES

In the two embodiments described above, the endoscope 200 is described to be the 3D endoscope; however, a technology according to the embodiment is not limited to the 3D endoscope and can be similarly widely applied to a two-dimensional endoscope including one imaging system.

In addition, In the two embodiments and the modification examples described above, an example of a case where the endoscope 200 is a medical rigid endoscope is described; however, the endoscope 200 can be similarly applied to a medical soft endoscope. In addition, the endoscope 200 is not limited to the medical endoscope and can also be applied to an industrial endoscope. In this case, a technology according to the embodiments and the modification examples can be used in a state in which an observation target and an instrument used with the industrial endoscope are distinguished based on a characteristic such as color in an image.

As described above, of the technology described in the embodiments, control mainly described by the flowchart can be realized by using a program. The program can be installed in a circuit such as the FPGA. In addition, in a case of an operation in the CPU or the like, the program may be stored in a recording medium or a recording unit, for example. Various methods may be used to perform recording to the recording medium or the recording unit. The recording may be performed at the time of product delivery, or the recording may be performed by using a distributed recording medium or using download via internet.

In addition, regarding methods of various kinds of determination of extracting the interference candidate area, selecting the interference area, or the like in the image process, for example, the embodiments described above are provided as examples, and various methods can be employed for such determination. Here, in the methods of various kinds of determination, the determination is not limited to simple determination based on the threshold value or the like as in the embodiments described above, and determination based on artificial intelligence or the like built on machine learning such as deep learning may be employed, for example.

In addition, the image processing apparatus according to the embodiments is not limited to the endoscope and can also be applied to a microscope, industrial equipment for inspection or the like, various medical observation apparatuses or the like.

Additional advantages and modifications will readily occur to those skilled in the art. Therefore, the invention in its broader aspects is not limited to the specific details, and representative devices shown and described herein. Accordingly, various modifications may be made without departing from the spirit or scope of the general inventive concept as defined by the appended claims and their equivalents.

What is claimed is:

1. An image processing apparatus for a three-dimensional endoscope, the image processing apparatus comprising:
    an image acquisition circuit configured to acquire a pair of images captured by using the endoscope;
    an interference area setting circuit configured to set, on an image among the pair of images, an interference area which is different from an observation target in the image with respect to a first characteristic, the first characteristic being a characteristic relating to color; and
    an interference area corrector configured to perform correction on the image, the correction comprising (i) specifying pixels in the image corresponding to the interference area as processing targets, and (ii) performing image processing to reduce luminance values of the pixels in the image specified as the processing targets,
    wherein the interference area setting circuit includes:

an interference candidate area extractor configured to extract at least one interference candidate area based on the first characteristic, and an interference area selector configured to select the interference area from the at least one interference candidate area based on positional information of the at least one interference candidate area in the image and an occupation percentage of areas having pixels with luminance values equal to or higher than a threshold value in the at least one interference candidate area, and wherein the interference area selector is configured to select, as the interference area, an interference candidate area that is in contact with a side of the image and that extends from a peripheral edge of the image towards an inside of the image.

2. The image processing apparatus according to claim 1, wherein the interference candidate area extractor is configured to use chroma information as the first characteristic.

3. The image processing apparatus according to claim 1, wherein the interference candidate area extractor is configured to use hue information as the first characteristic.

4. The image processing apparatus according to claim 1, wherein the interference area selector is configured to select the interference area from the at least one interference candidate area based on a size of the at least one interference candidate area.

5. The image processing apparatus according to claim 1, wherein the correction further comprises performing image processing to reduce chroma of the interference area.

6. The image processing apparatus according to claim 1, wherein the interference area corrector is configured to determine the threshold value based on a histogram of luminance values of pixels in the at least one interference candidate area.

7. The image processing apparatus according to claim 1, wherein the interference area setting circuit is further configured to set, on each image of the pair of images, the interference area to include an area captured only on the image of the pair of images.

8. The image processing apparatus according to claim 7, wherein the correction further comprises performing image processing to reduce chroma of the interference area.

9. An endoscope system comprising:
the image processing apparatus according to claim 1; and
the endoscope.

10. The image processing apparatus according to claim 1, wherein the interference area comprises an area of a procedure tool.

11. An image processing apparatus for a three-dimensional endoscope, the image processing apparatus comprising:

an image acquisition circuit configured to acquire a pair of images captured by using the endoscope; and a processor, wherein the processor is configured to:

set, on an image among the pair of images, an interference area which is different from an observation target in the image with respect to a first characteristic, the first characteristic being a characteristic relating to color, and the interference area being set by (i) extracting at least one interference candidate area based on the first characteristic, and (ii) selecting the interference area from the at least one interference candidate area based on positional information of the at least one interference candidate area in the image and an occupation percentage of areas having pixels with luminance values equal to or higher than a threshold value in the at least one interference candidate area, and perform correction on the image, the correction comprising (i) specifying pixels in the image corresponding to the interference area as processing targets, and (ii) performing image processing to reduce luminance values of the pixels in the image specified as the processing targets, and wherein the selecting the interference area comprises selecting, as the interference area, an interference candidate area that is in contact with a side of the image and that extends from a peripheral edge of the image towards an inside of the image.

* * * * *